United States Patent [19]

Folkers et al.

[11] Patent Number: 4,824,669
[45] Date of Patent: Apr. 25, 1989

[54] FORMULATIONS OF COENZYME $Q_{10}$ FOR INTRAVENOUS USE

[75] Inventors: Karl Folkers, Austin, Tex.; Kazumasa Muratsu, Fukuoka, Japan

[73] Assignee: Board of Regents, The University of Texas System, Austin, Tex.

[21] Appl. No.: 31,487

[22] Filed: Mar. 27, 1987

Related U.S. Application Data

[63] Continuation-in-part of Ser. No. 722,861, May 11, 1985, abandoned.

[51] Int. Cl.$^4$ .................. A61K 31/12; A61K 31/685; A61K 37/48
[52] U.S. Cl. .................................... 424/94.1; 514/690
[58] Field of Search ........................... 424/94; 514/690

[56] References Cited

U.S. PATENT DOCUMENTS

| | | | |
|---|---|---|---|
| 4,068,003 | 1/1978 | Miyata | 424/331 |
| 4,156,718 | 5/1979 | Blizhakov | 424/94 |
| 4,325,942 | 4/1982 | Taki et al. | 424/94 |
| 4,483,873 | 11/1984 | Ohashi et al. | 424/331 |
| 4,617,187 | 10/1986 | Okuyama et al. | 424/94 |

OTHER PUBLICATIONS

Lucker, et al., Biomedical and Clinical Aspects of Coenzyme Q, vol. 4:143-151 (1984).
Sunamori, et al., Biomedical and Clinical Aspects of Coenzyme Q, 54:333-342 (1984).
Turco and King, Remington Pharmaceutical Sciences, 16th Edition, pp. 1488-1497 (1980).
Yamaguchi, J. Pharm. Pharmacol., 36:768-769 (1984).
Eisai, Co. Ltd., Chem. Abstracts, 100:367, No. 100, Abstract No. 145017d (1984).
European Patent Application Publication No. 0132821. Folkers, C. & En., Apr. 21, 1986, pp. 27-56.
Yamaguchi, Pharmaceuticals, 102:473, Abstract No. 32098d (1985).
Kanazawa and Takahashi, Biomedical and Clinical Aspects of Coenzyme Q, 3:31-42 (1981).
Kishi, et al., Biomedical and Clinical Aspects of Coenzyme Q, 3:67-78 (1981).
Page, et al., Archives Biochem. Biophy., 85:476 (1980).

*Primary Examiner*—John Kight
*Assistant Examiner*—Nathan M. Nutter
*Attorney, Agent, or Firm*—Arnold, White & Durkee

[57] ABSTRACT

The present invention comprises a stable and non-toxic coenzyme $Q_{10}$ formulation suitable for intravenous administration to an animal to produce clinically effective blood levels of coenzyme $Q_{10}$. Clinically effective blood levels of coenzyme $Q_{10}$ are generally agreed to be between about 2 ug/ml and about 4 ug/ml. The formulation consists essentially of a clinically accepted fatty emulsion having an oil phase and coenzyme $Q_{10}$ dissolved in the oil phase. The formulation preferably contains coenzyme $Q_{10}$ at a level between about 7.5 ug/ml and about 30 ug/ml. The clinically accepted fatty emulsion comprises at least one vegetable oil, preferably corn oil, peanut oil, safflower oil, olive oil or soybean oil.

19 Claims, No Drawings

FORMULATIONS OF COENZYME $Q_{10}$ FOR INTRAVENOUS USE

CROSS REFERENCE TO RELATED APPLICATIONS

This is a continuation-in-part of Serial No. 722,861, filed May 11, 1985 and now abandoned, expressly incorporated by reference herein.

BACKGROUND OF THE INVENTION

This invention relates to new formulations comprising coenzyme $Q_{10}$ ($CoQ_{10}$) in fat emulsions for use in clinical medicine. The fat emulsions used are those commonly administered intravenously to patients in clinical practice. Based on pharrmacokinetic data from healthy human subjects orally administered with $CoQ_{10}$ (2,3-dimethoxy-5-methyl-6-decaprenyl benzoquinone), there is very slow absorption of $CoQ_{10}$ as monitored, for example, by blood plasma levels. There is a lag time of about one hour before an increase in the plasma level of $COQ_{10}$ is detected. Subsequently there was a maximum increase in the plasma level of $CoQ_{10}$ after about 5 to 6 hours, which was relatively stable until up to about 24 hours when a second peak of plasma $CoQ_{10}$ was measured. This slow absorption and the second maximum plasma level may relate to the insolubility of $CoQ_{10}$ in aqueous media. The extreme lipophilicity of $CoQ_{10}$ also may explain why as much as 62% of an orally administered dose has been recovered from the feces during a study period of 10 days. If feces were analyzed over a longer period, an even higher level of excretion of unchanged $CoQ_{10}$ would be expected. The overall absorption of orally administered $CoQ_{10}$ is expected to be in the range of 10-20% (Lucker et al., *Biomedical and Clinical Aspects of Coenzyme Q*. V 4; K. Folkers and Y. Yamamura, eds., Elsevier/North-Holland Biomedical Press, Amsterdam, 143-151, (1984)).

Sunamori et al. investigated the clinical application of $CoQ_{10}$ to patients having coronary artery by-pass graft surgery (*Biomedical and Clinical Aspects of Coenzyme Q*. V 4, K. Folkers and Y. Yamamura, eds., Elsevier/North-Holland Biomedical Press, Amsterdam, 333-342 (1984)). Cardioplegia does not provide complete myocardial protection from ischemia, and a certain amount of perioperative myocardial infarction is inevitable, despite the generally low incidence of infarction associated with coronary artery bypass surgery. Sunamori et al. endeavored to determine whether the administration of $CoQ_{10}$ would protect cardiac function in clinical coronary artery revascularization. They reported that the oral administration of $CoQ_{10}$ failed to allow satisfactory tissue concentrations of $CoQ_{10}$ under medically acceptable conditions for such surgery.

Approximately 40% of all drugs administered to patients in hospitals are given in the form of injections. Intravenous formulations now have a major role as vehicles for drugs. Intravenous formulations are finding a greater use in the administration of drugs, because of dependability, accuracy, convenience, avoidance of the gastric irritation potential of orally administered drugs, and the importance of continuous as well as intermittent drug therapy. Techniques for providing intravenous administrations have improved steadily in the last decade, and the use of such intravenous formulations has been anually increasing at the rate of about 40% (*Remington's Pharmaceutical Sciences*, 16th Ed., A. Osol, Ed., Mack, Easton, Pa., (1980), pp. 1488-1497).

Coenzyme $Q_{10}$, being highly hydrophobic, is essentially insoluble in aqueous solutions. For $CoQ_{10}$ to be parenterally administered, it must be contained in a stable formulation compatible with, for example, intravenous injection. One approach to prepare an intravenous formulation of coenzyme $Q_{10}$ in an aqueous medium requires the inclusion of one or more surfactants and other entities which would allow the creation of a dispersion of particles of coenzyme $Q_{10}$ in an aqueous medium. There are many difficulties associated with this approach. A prominent difficulty is related to the fact that $CoQ_{10}$ is a solid at temperatures below about 50° C. The dispersion of solid particles of $CoQ_{10}$ in an aqueous medium involves difficulties in the preparation of a safe formulation with a stability up to about two years for clinical application. Such solid particle dispersions have been explored, but on standing, particles containing $CoQ_{10}$ fall to the bottom of the container, and redispersion by stirring or shaking definitely does not meet the requirements for medical use. Successful formulations should have a stability of up to about two about years to become established for clinical use. The second prominent difficulty is having a formulation which, on intravenous administration, does not lead to particle separation or precipitation within the blood stream. Such a separation would be detrimental to blood flow and potentially be life-threatening.

It is unsafe and improper for pharmacists to make experimental formulations of $CoQ_{10}$ of unproven quality and to provide such formulations to physicians for intravenous administration within days or a week or more.

Others have attempted to produce fatty emulsions of $CoQ_{10}$. Yamaguchi et al. (J. Pharm. Pharmacol., (1984), 36:768-769) describe a fat emulsion of coenzyme $Q_{10}$ (100 $\mu$g(microgram)/ml), phospholipid, glycerol, soybean oil and water.

An Eisai Co. Ltd. reference (Chem. Abstracts, 100:367, No. 100:145017d) describes an injectable emulsion containing $CoQ_{10}$ (ubidecarenone, 1 mg/ml), lecithin, ethanol, MACROGOL 400, sorbitol and water. European Patent Application Publication No. 0132821 described aqueous solutions comprising lipid-soluble substances such as coenzyme $Q_{10}$ (preferably between 1 mg/ml and 10 mg/ml), hydrogenated lecithin and neutral amino acids.

U.S. Pat. No. 4,068,003 (Miyata) described an injectable emulsion containing coenzyme $Q_{10}$ (10 mg/ml), detergemt Nikkol HCO-60, sesame oil, sodium chloride, propylene glycol and phosphate buffer.

U.S. Pat. No. 4,156,718 (Bliznakov) describes a treatment for reversal of immunological senescance involving administration of $CoQ_{10}$. Oral administration of $CoQ_{10}$ was preferred for humans and intravenous for lower animals. An emulsion comprising $CoQ_{10}$ (125 $\mu$g/ml, 5% glucose solution and detergent 0.4% Tween 20 (polyoxyethylene sorbitol monolaureate)).

No $CoQ_{10}$ emulsion has been heretofore produced which is free of additions such as detergents or surfactants and having levels of $CoQ_{10}$ sufficiently high to be clinically effective yet low enough to avoid potential toxic effects of intravenous $CoQ_{10}$ excess.

SUMMARY OF THE INVENTION

The present invention comprises a stable and nontoxic coenzyme $Q_{10}$ formulation suitable for intravenous administration to an animal to produce clinically effective blood levels of coenzyme $Q_{10}$. Clinically effective and therepeutic blood levels of coenzyme $Q_{10}$ are generally agreed to be between about 2 µg/ml and about 4 µg/ml. The $CoQ_{10}$ formulation of the present invention consists essentially of a clinically accepted fatty emulsion having an oil phase and coenzyme $Q_{10}$ dissolved in the oil phase. The formulation preferably contains coenzyme $Q_{10}$ at a level between about 7.5 µg/ml and about 30 µg/ml. The clinically accepted fatty emulsion comprises at least one vegetable oil, preferably corn oil, peanut oil, safflower oil, olive oil or soybean oil.

Clinically accepted fatty emulsions usable in the practice of the present invention include emulsions such as Liposyn, Soyacal, Intralipid or Travemulsion, for example. The formulation of the present invention is preferably essentially free of exogenous detergent.

The present invention also comprises a method for preparing a stable and non-toxic coenzyme $Q_{10}$ formulation suitable for intravenous administration to an animal to produce clinically effective blood levels of coenzyme $Q_{10}$. This method involves thoroughly mixing a clinically accepted fatty emulsion having an oil phase with an amount of coenzyme $Q_{10}$ sufficient to result in a formulation having a coenzyme $Q_{10}$ concentration between about 7.5 µg/ml and about 30 µg/ml. The coenzyme $Q_{10}$ is most preferably initially in a vegetable oil solution and the solution is thoroughly mixed with the clinically established fatty emulsion. The thorough mixing may be accomplished by many means well-known in the field and may, for example, involve sonication or repeated passage through a small orifice such as that of a syringe needle.

The present invention also includes a method for raising blood levels of coenzyme $Q_{10}$ to clinically effective levels in an animal. This method comprises first obtaining a stable and non-toxic formulation, preferably free of exogenous detergent and comprising a clinically accepted fatty emulsion and coenzyme $Q_{10}$ at a concentration between about 7.5 µg/ml and about 30 µg/ml. The next step of the method is intravenously administering said formulation to the animal to achieve blood levels of coenzyme $Q_{10}$ of between about 2 µg/ml and about 4 µg/ml.

DESCRIPTION OF THE PREFERRED EMBODIMENT

Coenzyme $Q_{10}$ is essentially insoluble in aqueous media. This insolubility is related to the 50-carbon atom isoprenoid side chain, of hydrocarbon nature, as shown in the following structure of coenzyme $Q_{10}$.

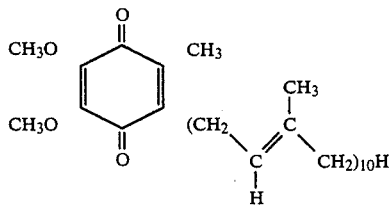

Pharmacokinetic data has shown that intestinal absorption of coenzyme $Q_{10}$ is slow and inefficient in human subjects. A lag time of about one hour occurs before an increase in the plasma level of $CoQ_{10}$ can be detected. There are two peaks in plasma $CoQ_{10}$ levels with the second peak appearing after about 24 hours. This slow absorption is likely to be related to the aqueous insolubility of $CoQ_{10}$ because of its extreme lipophilicity. Absorption of orally administered $CoQ_{10}$ is variable and in the range of only about 10-20%. A formulation of coenzyme $Q_{10}$ for intravenous use which meets high standards of safety and stability has been devised. This formulation was prepared by combining pure coenzyme $Q_{10}$ with fat emulsions which are clinically accepted and are generally made with a vegetable oil such as soybean oil. Although soybean oil naturally contains coenzyme $Q_{10}$, the level of $CoQ_{10}$ is but a trace which has little clinical significance.

The intravenous $Q_{10}$ formulations of the present invention allow the delivery of precise amounts of $CoQ_{10}$ into the blood stream for transport to organs such as liver and heart and other tissues for therapeutic benefit. The extreme lipophilicity of $CoQ_{10}$ is a likely basis of its variable gastrointestinal absorption and for uncertain therapeutic response to oral $CoQ_{10}$. Oral formulations of $CoQ_{10}$ may thus be ineffective for acute and life-threatening clinical situations. A prompt, precise and efficient distribution is frequently essential for patients to have the maximum benefit of the life saving and extending activity of $CoQ_{10}$.

A clinically effective and usable intravenous formulation of $CoQ_{10}$ should be stable at common ambient temperatures and remain essentially unchanged in dispersion characteristics for periods of at least a year, because this period would be about that required for preparation, analysis, shipment to distribution centers, shipment to and storage in hospitals until use, etc.

The dissolving of pure $CoQ_{10}$ in soybean oil and encapsulation of the dissolved $CoQ_{10}$ in sealed soft gelatin capsules has been earlier accomplished and such capsules have been in medical use for several years. These capsules consisted of $CoQ_{10}$ and soybean oil.

An object of the present invention is the achievement of an emulsion of $CoQ_{10}$ and soybean oil in an aqueous milieu with excellent dispersion and stability characteristics. Such a formulation has been produced and is safe and effective for medical use. This embodiment of the present invention is an emulsion consisting essentially of a dispersion of the $CoQ_{10}$ in soybean oil in an aqueous system which has excellent dispersion and stability characteristics.

Toward achieving such $CoQ_{10}$-soybean oil emulsions, it was desired to use commercially and medically accepted fat emulsions. Such emulsions were exemplified by INTRALIPID (Kabi-Vitrum of Emoryville, Calif. and Stockholm, Sweden); LIPOSYN (Abbott Laboratories, North Chicago, Ill.); SOYACAL (Alpha Therapeutic Corp., 555 Valley Blvd., Los Angeles, Calif.); and TRAVEMULSION (Travenol Labs, Inc., 1 Baxter Parkway, Deerfield, Ill.). These commercial fat emulsions for practical use in clinical medicine, were known to be acceptably safe and also to have a shelf storage life of up to two years or longer. Such medically useful and marketed fat emulsions generally contain 10-20% of a vegetable oil, which is commonly soybean oil, although safflower oil and other vegetable oils may be correspondingly useful and practical.

The simple combination of $CoQ_{10}$ with one of these commercial fat emulsions resulted in unstable formulations from which the $CoQ_{10}$ would too readily separate. The present inventors had earlier been involved with the clinical oral administration of $CoQ_{10}$ in soft gelatin capsules to a diversity of patients. These capsules typically contained 33.3 mg of pure $CoQ_{10}$ and about 400 mg of soybean oil. These capsules were manufactured by R.P. Scherer North American, P.O. Box 5600, Clearwater, Fla. 33518. The $CoQ_{10}$ in the capsules was produced by Kanegafuchi Chemical Industry, Inc. Ltd., Osaka Japan, *Biomedical and Clinical Aspects of Coenzyme Q*, V 3, K. Folkers and Y. Yamamura eds., Elsevier/North-Holland Biomedical Press, Amsterdam, 31–42 (1981)).

These oral capsules of $CoQ_{10}$-containing soybean oil literally consisted of "soybean oil fortified with $CoQ_{10}$", since the natural level of $CoQ_{10}$ in soybean oil was far to low to be clinically effective.

A medically accepted fat emulsion containing soybean oil also contains trace amounts of $CoQ_{10}$ from the soybean oil. An Intralipid formulation fortified with $CoQ_{10}$ and prepared by others was found to be pharmaceutically unacceptable because the $CoQ_{10}$ separated, as evidenced by a yellow "droplet-like" layer which was easily visible on the surface of the emulsion.

A stable, non-toxic and effective emulsified $CoQ_{10}$ preparation suitable for medical use was previously unavailable and the present invention involved the first preparation and use of such a preparation.

The present invention comprises an emulsion of $CoQ_{10}$ which is stable, medically safe and therapeutically effective. This fat emulsion most preferably consists essentially of one or more vegetable oils and about 7.5 $\mu g/ml$ to about 30 $\mu g/ml$ CoQ10. The emulsion is preferably free of detergent ad surfactant additives. At $CoQ_{10}$ levels below about 7.5 $\mu g/ml$, too large a volume of an emulsion is intravenously required to attain effective therapeutic $CoQ_{10}$ blood levels. At $CoQ_{10}$ levels above about 30 $\mu g/ml$, the emulsions tend to be unstable so that the $CoQ_{10}$ may separate during storage and/or possibly during use. Separation of $CoQ_{10}$ from an intravenously administered emulsion could lead to dangerous emboli formation. Separation of $CoQ_{10}$ during storage would result in clinical unacceptability.

Average normal and therapeutic human blood levels of $CoQ_{10}$ are generally agreed to be about 1 $\mu g/ml$ and 2–4 $\mu g/ml$ respectively. Table 1 shows normal levels, suggested therapeutic levels and related total amounts of $CoQ_{10}$ in human blood.

TABLE 1

| Human Blood $CoQ_{10}$ Levels | | | |
|---|---|---|---|
| Normal Levels | | Therapeutic Levels | |
| per ml | per body | per ml | total per body |
| 1 ug | 5 mg | 2 ug | 10 mg |
| | | 3 ug | 15 mg |
| | | 4 ug | 20 mg |

It is known from the existing clinical data from the daily oral administration of 100 mg of $CoQ_{10}$ to patients (3 capsules of 33.3 mg each in soybean oil), that blood levels in the range of about 2–4 $\mu g/ml$ whole blood may be achieved. These blood levels on daily oral administration of 3 capsules vary between about 1.5 and 4 $\mu g/ml$ whole blood, depending upon the initial control level, the variation of oral absorption, patient compliance, etc. If a blood level of 3 $\mu g/ml$ of whole blood is achieved on therapy, the amount of $CoQ_{10}$ in the total blood volume would be about 15 mg. The gastrointestinal absorption of $CoQ_{10}$ from 3 capsules/day is about 15% or 15–20% according to Lucker et al. (citation under Background of the Invention). However, as mentioned earlier herein, oral administration of $CoQ_{10}$ is undependable and sometimes difficult.

It is biochemically sound that any patient in cardiac distress and with a deficiency of $CoQ_{10}$ at the receptors, for example, of the $CoQ_{10}$-dependent enzymes could achieve prompt saturation of the empty receptors by treatment with an intravenous formulation of $CoQ_{10}$. This is in contrast to the uncertain and time consuming achievement of saturation subsequent to oral $CoQ_{10}$ administration. Consequently, the intravenous formulations of the present invention should be medically useful for a diversity of patients, particularly those in cardiac distress. This is in contrast to oral formulations which may give variable results and may not be possible to use with effectiveness.

The examples contained herein illustrate the design and preparation of intravenous formulations of $CoQ_{10}$ for use in clinical medicine. The vegetable oils present in our exemplary formulations have been safflower oil and soybean oil. The use of other vegetable oils such as corn oil, peanut oil, olive oil, for example, are within the scope of this invention. The fact that corn oil and wheat germ oil, as examples, contain coenzyme $Q_9$ rather than coenzyme $Q_{10}$ does not exclude their use in the preparation of fat emulsions, because the level of coenzyme $Q_9$ in these oils is a trace which would have little metabolic significance. For example, corn oil is used commonly in foods and diets and the trace levels of coenzyme $Q_9$ are metabolically and therapeutically meaningless.

The intravenous formulations of the present invention may be used, for example, to introduce 15 mg, 10 mg and 5 mg of $CoQ_{10}$ into the total body blood volume by intravenous administration of about 500 ml containing 30 $\mu g/ml$, 15 $\mu g/ml$ and 7.5 $\mu g/ml$, respectively, of $CoQ_{10}$. On the basis that the control blood level of $CoQ_{10}$/total body volume is 5 mg, then the total body volume would contain 20 mg, 15 mg, and 10 mg, respectively, after the intravenous administration of the three formulations.

A preferred technique of preparing formulations of the present invention involved adding 1 ml of a fat emulsion such as Intralipid, Liposyn, Soyacal, and Travemulsion to each of three tubes. With a microsyringe, 1 $\mu l$ of soybean oil containing 30 $\mu g$, 15 $\mu g$ and 7.5 $\mu g$ of $CoQ_{10}$, respectively, was added to each of the three tubes containing 1 ml the fat emulsion. The microliter of soybean oil containing these three amounts of $CoQ_{10}$ was easily visible by the yellow color on the surface of the fat emulsion. The contents of these tubes were cooled to less than about 5° C. and were then sonicated for about 5 seconds in an ice bath. The sonicated $CoQ_{10}$-fat emulsion was then drawn into a first syringe through the syringe needle. The needle of the first syringe was then connected to the needle of a second syringe. The $CoQ_{10}$-fat emulsion was then passed back and forth through the needles from the first syringe to the second syringe, and this mixing was repeated about 10 times. The needles of the two syringes were connected through a rubber stopper or a tubing, which sufficed for this laboratory scale preparation.

At the concentrations of 30, 15 and 7.5 $\mu g/ml$ of commercial fat emulsion, the $CoQ_{10}$ did not visibly separate to the surface. The stability of these microconcentrations of $CoQ_{10}$ in the emulsion, suggested that the $CoQ_{10}$ was dissolved in the "micro-spheres" of oil in the emulsion.

It was known that $CoQ_{10}$ is stable in, for example, the soybean oil contained in soft gelatin capsules, for up to 6 years. The $CoQ_{10}$-fat emulsion formulation of the present invention should be as stable as the fat emulsions themselves. This stability of the commercial emulsions included in the formulations of the present invention was known to be sufficient to allow them to be marketed for intravenous use in clinical medicine.

The above-described preparation procedure was on a laboratory scale and may be appropriately modified and scaled up to allow the production of unlimited amounts of the $CoQ_{10}$-fat emulsion for commercial use. The changes in procedure between the laboratory appropriate for factory scale production are within the scope of this invention.

These three particular exemplary formulations of the present invention will allow the introduction of $CoQ_{10}$ into the blood of patients to levels of 2, 3 and 4 µg/ml, respectively, for a total amount of $CoQ_{10}$/total body volume of blood of, for example, about 10, 15 and 20 mg, respectively.

Coenzyme $Q_{10}$-fat emulsions have been prepared at three exemplary concentrations for intravenous administration to patients. These formulations have clinical flexibility, and should allow the achievement of blood levels at least comparable to what may be achieved by administration of oral formulations but in a rapid, dependable and safe manner. It is common in clinical medicine to intravenously administer up to 500 ml and even up to 1000 ml of the marketed fat emulsions referred to above. Increases of 5, 10 and 15 mg of $CoQ_{10}$ in the total blood volume may readily be achieved by adjusting the concentration of $CoQ_{10}$ in the fat emulsion or by adjusting the volume of the administered formulation. These two variables allow flexibility for particular patients. Since the normal level of $CoQ_{10}$ in the blood volume is about 5 mg, this level may be taken into account in the selection of the concentration of $CoQ_{10}$ in a formulation of the present invention and the volume of the formulation to be intravenously administered.

The level of $CoQ_{10}$ in the fat emulsion may be critical for success on the basis that too much $CoQ_{10}$ may result in separation of the $CoQ_{10}$, and levels in the critical range allow the $CoQ_{10}$ to be retained or dissolved in the emulsified oil particles.

Since $CoQ_{10}$ has a clinical record of safety of over a decade, and a record of stability of up to 6 years in encapsulated soybean oil, and since the commercial fat emulsions with soybean oil, primarily, have a record of stability and safety, the $CoQ_{10}$-fat emulsions of the present invention provide assurance of safety for intravenous administration and efficacy of therapeutic benefit, particularly, for example, in cardiology.

To appreciate the importance and utility of the intravenous $CoQ_{10}$ formulations of the present invention, it is helpful to understand the limitations and negative aspects of oral formulations of $CoQ_{10}$. As mentioned elsewhere herein, oral $CoQ_{10}$ has not been successfully orally administered to cardiac patients having by-pass surgery. The seriousness, timeliness, and survival rate involved in this surgery is not compatible with the variability and uncertainty of oral absorption of $CoQ_{10}$. Cardiac patients with acute infarction or with chest pains associated with infarction should have rapid and effective treatment. Oral therapy with $CoQ_{10}$ does not meet the therapeutic requirements for such crises.

Patients with Class IV cardiomyopathy, who have severe disease, and are in a life-threatening situation are only questionably benefitted because of the very slow and erratic absorption by oral treatment with $CoQ_{10}$. Cardiac patients with acute ischemia should best benefit from prompt and effective intravenous administration of $CoQ_{10}$ in contrast to the uncertainties and low degrees of absorption characteristic of oral $CoQ_{10}$ administration. Infants and children in cardiac distress, and who may not be able to swallow normally oral preparations of $CoQ_{10}$, and patients who are unconscious, comatose or severely injured may be effectively treated intravenously, but not by the oral route.

Changes may be made in the construction, operation and arrangement of the various elements, steps and procedures described herein without departing from the concept and scope of the invention as defined in the following claims.

What is claimed is:

1. A stable and non-toxic coenzyme $Q_{10}$ formulation suitable for intravenous administration to an animal to produce clinically effective blood levels of coenzyme $Q_{10}$, the formulation consisting essentially of a clinically accepted fatty emulsion having an oil phase and coenzyme $Q_{10}$ dissolved in the oil phase, the formulation containing coenzyme $Q_{10}$ at a level between about 7.5 µg/ml and about 30 µg/ml.

2. The formulation of claim 1 wherein the fatty emulsion comprises at least one vegetable oil.

3. The formulation of claim 2 wherein the vegetable oil is at least one of corn oil, peanut oil, safflower oil, olive oil or soybean oil.

4. The formulation of claim 1 wherein the clinically accepted fatty emulsion comprises from 10% to 20% vegetable oil.

5. The formulation of claim 1 wherein the clinically accepted blood levels of coenzyme $Q_{10}$ are between about 2 µg/ml and about 4 µg/ml.

6. The formulation of claim 1 wherein the formulation is defined further as being essentially free of exogenous detergent.

7. A method for preparing a stable and non-toxic coenzyme $Q_{10}$ formulation suitable for intravenous administration to an animal to produce clinically effective blood levels of coenzyme $Q_{10}$, the method comprising thoroughly mixing a clinically accepted fatty emulsion having an oil phase with an amount of coenzyme $Q_{10}$ sufficient to result in a formulation having a coenzyme $Q_{10}$ concentration between about 7.5 µg/ml and about 30 µg/ml.

8. The method of claim 7 wherein the fatty emulsion comprises at least one vegetable oil.

9. The method of claim 8 wherein the vegetable oil is at least one of corn oil, peanut oil, safflower oil, olive oil or soybean oil.

10. The method of claim 8 wherein the clinically accepted fatty emulsion comprises from 10% to 20% vegetable oil.

11. The method of claim 7 defined further wherein the coenzyme $Q_{10}$ is initially in a vegetable oil solution and the solution is thoroughly mixed with the clinically accepted fatty emulsion.

12. The method of claim 7 wherein the thorough mixing comprises sonication or repeated passage through a small orifice.

13. The method of claim 7 wherein the clinically effective blood levels of coenzyme $Q_{10}$ are between about 2 µg/ml and about 4 µg/ml.

14. The method of claim 7 wherein the formulation is defined further as being essentially free of exogenous detergent.

15. A method for raising blood levels of coenzyme $Q_{10}$ to clinically effective levels in an animal, the method comprising:

obtaining a stable and non-toxic formulation comprising a clinically accepted fatty emulsion and coenzyme $Q_{10}$ at a concentration between about 7.5 $\mu$g/ml and about 30 $\mu$g/ml; and intravenously administering said formulation to the animal to achieve blood levels of coenzyme $Q_{10}$ of between about 2 $\mu$g/ml and about 4 $\mu$g/ml.

16. The method of claim 15 wherein the fatty emulsion comprises at least one vegetable oil.

17. The method of claim 16 wherein the vegetable oil is at least one of corn oil, peanut oil, safflower oil, olive oil or soybean oil.

18. The method of claim 15 wherein the clinically accepted fatty emulsion comprises from 10% to 20% vegetable oil.

19. The method of claim 15 wherein the formulation is defined further as being essentially free of exogenous detergent.

* * * * *